United States Patent
Yoshimi et al.

(10) Patent No.: US 6,386,051 B1
(45) Date of Patent: May 14, 2002

(54) LOAD DETECTION SENSOR UNIT FOR BEDDING WITH SINGLE OUTPUT LINE

(75) Inventors: Tomohisa Yoshimi, Gamagori; Masahiko Ito, Nagoya, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/499,012

(22) Filed: Feb. 4, 2000

(30) Foreign Application Priority Data

Mar. 15, 1999 (JP) .................................... 11-068865

(51) Int. Cl.⁷ .......................... G01D 7/00; G01L 3/00
(52) U.S. Cl. ............................................... 73/862.046
(58) Field of Search ................... 73/841, 172, 862.046, 73/862.041, 862.043; 5/618, 713, 706, 508; 340/573, 575; 250/231.1

(56) References Cited

U.S. PATENT DOCUMENTS

| | | | |
|---|---|---|---|
| 5,010,772 A | * | 4/1991 | Boruland et al. ......... 73/862.04 |
| 5,408,754 A | * | 4/1995 | Raab ............................ 33/503 |
| 5,571,973 A | * | 11/1996 | Taylot ................... 73/862.046 |
| 5,993,400 A | * | 11/1999 | Rincoe et al. .............. 600/595 |
| 6,105,187 A | * | 8/2000 | Gnjatovic ...................... 5/618 |

FOREIGN PATENT DOCUMENTS

| JP | 2-41158 | 2/1990 |
|---|---|---|

* cited by examiner

*Primary Examiner*—Max Noori
*Assistant Examiner*—Octavia Davis
(74) *Attorney, Agent, or Firm*—Law Offices of David G. Posz

(57) ABSTRACT

A load detection sensor unit for a bedding comprises a plurality of load detection devices and a signal processing circuit which is connectable to an external electrical unit. The signal processing circuit includes a plurality of analog switches connected to the load detection devices, a single output line connected to the analog switches, and a load resistor connected to the single output lines. The analog switches are turned on sequentially so that output signals of the load detection devices are serialized and transmitted to the external electrical unit through the single output line. The load detection devices and the signal processing circuit are formed integrally on an elastic film and connected through elastic conductors.

13 Claims, 2 Drawing Sheets

LOAD DETECTION SENSOR UNIT FOR BEDDING WITH SINGLE OUTPUT LINE

CROSS REFERENCE TO RELATED APPLICATION

This application relates to and incorporates herein by reference Japanese Patent Application No.11-68865 filed on Mar. 15, 1999.

BACKGROUND OF THE INVENTION

1. Field of the Invention

The present invention relates to load detection sensor units for beddings, and particularly to a load detection sensor unit for use on an air mat.

2. Related Art

JP-A-2-41158 discloses an air mat which is comprised of a plurality of air cells. The pressure of the air cells is varied at regular time intervals to restrict bedsores of sleepers such as aged persons or sick persons lying on the air mat for months. The pressure is varied uniformly in all the air cells. Therefore, this air mat cannot restrict the bedsores from growing.

It is proposed to use a load detection sensor unit comprising a plurality of load detection devices, so that a posture of a sleeper is determined based on output signals of the detection devices. It is however impractical to extend signal output lines from the detection devices to a signal processing circuit external from the load detection sensor unit.

If the load detection sensor unit is used on the air mat of the above type, it must be constructed with an elastic film to change its shape with changes in the shape of air cells. Further, if an electrical circuit of the signal processing circuit which is generally rigid is integrated with the load detection devices, electrical connections between the elastic film and the electrical circuit must be ensured.

SUMMARY OF THE INVENTION

It is therefore an object of the present invention to provide a load detection sensor unit which requires less electrical signal lines for connection with an external electrical unit.

It is another object of the present invention to provide a load detection sensor unit which ensures good electrical connections between load detection devices made of an elastic film and an electrical circuit integrated with load detection devices.

According to the present invention, a load detection sensor unit for a bedding includes a plurality of load detection devices arranged as a part of the bedding for producing output signals variable with load applied thereto by a sleeper, respectively, and switches for turning on and off a transmission of the output signals of the detection devices to the signal line. The switches are turned on sequentially to serialize the output signals of the detection devices to be transmitted serially to an external electrical unit through a single signal line.

Preferably, the load detection devices are formed integrally with a signal processing circuit including the switches and the single signal line on an elastic film. The load detection devices and the signal processing circuit are electrically connected to each other through elastic conductors.

BRIEF DESCRIPTION OF THE DRAWINGS

Other objects, features and advantages of the present invention will become more apparent from the following detailed description made with reference to the accompanying drawings. In the drawings.

DETAILED DESCRIPTION OF THE PREFERRED EMBODIMENT

Figure 1:
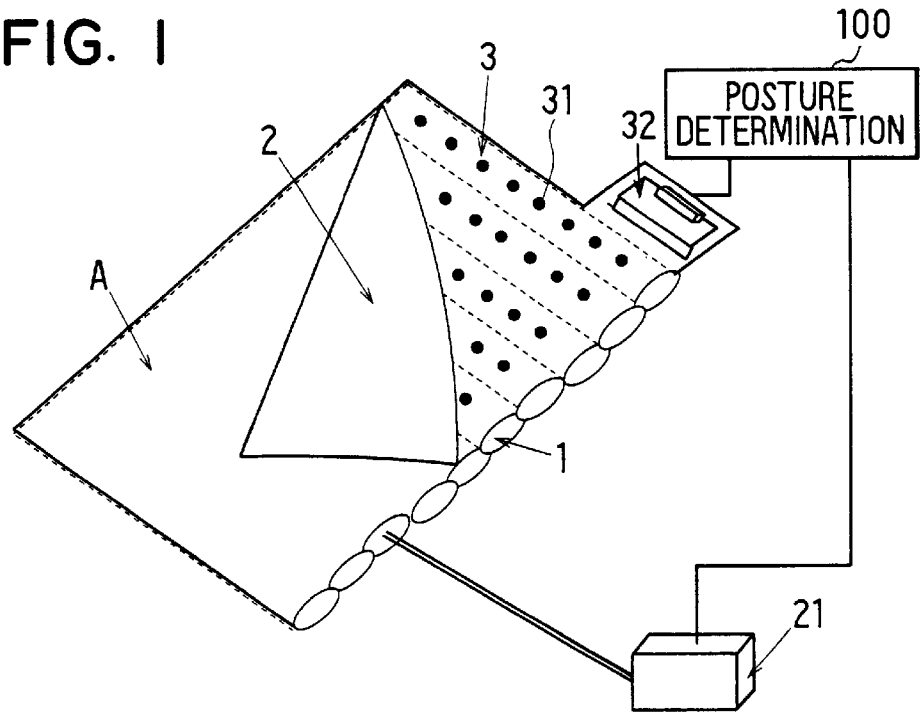
FIG. 1 is a perspective view showing a load detection sensor unit for bedding according to an embodiment of the present invention.

Referring to FIG. 1, a bedding A comprises an air mat 1 to be placed on a bed frame (not shown), a sheet 2 covering the mat 1, and a load detection sensor unit 3 disposed between the air mat 1 and the sheet 2. The air mat 1 is comprised of a plurality of air tubes or cells. The inside pressure of each cell is regulated to a predetermined pressure by air supplied from an air pump.

The load detection sensor unit 3 sandwiched between the air mat l and the sheet 2 is comprised of a number of (210, for instance) load detection devices 31 arranged uniformly over each air cell. Each detection device 31 is a type which varies its resistance in accordance with the load applied thereto at a contact part between the air mat 1 and a sleeper on the mat 1. The load detection sensor unit 3 has a signal processing circuit 32 for producing output signals to an external electrical device such as a posture determination unit 100 which determines a posture of a sleeper from output signals of the detection devices 31 and displays the determined sleeping posture. That is, the posture determination unit 100 is constructed to calculate loads of the sleeper with respect to each part of the body of the sleeper and display the determined sleeping posture thereon. The air pump is preferably controlled by the posture determination unit 100 to regulate the inside pressure of the air cells with respect to each part of the body of the sleeper based on the determined sleeping posture. The inside pressure of the air cells under or around the bedsores are reduced so that the air cells do not contact the bedsores.

Figure 2A:
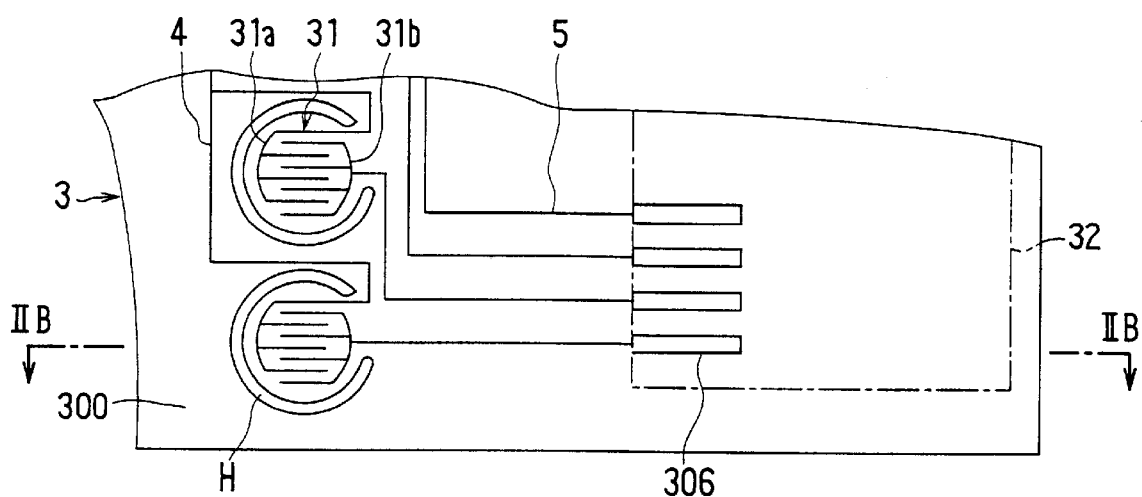
FIG. 2A is a plan view showing a part of the load detection sensor unit shown in FIG. 1.
Figure 2B:
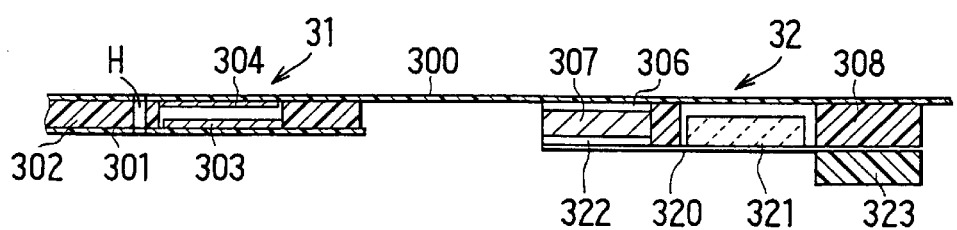
FIG. 2B is a sectional view showing the load detection sensor unit taken along line IIB—IIB in FIG. 2A.

The load detection sensor unit 3 is constructed as shown in FIGS. 2A and 2B. That is, each detection device 31 has a pair of comb-like interleaved electrodes 31a and 31b arranged to face each other. The electrode 31a is connected to a common power source (not shown) through a power supply line 4, and the electrode 31b is connected to a corresponding electrode terminal 306 of the signal processing circuit 32 through a signal output line 5.

The detection devices 31 and the signal processing circuit 32 are formed on a base film 300 printed with conductive patterns in a predetermined shape. The conductive patterns include the power supply line 4 connected to the electrodes 31a, the signal output lines 5 connected to the electrodes 31b, and the electrode terminals 306 connected to the signal output lines 5.

A pressure-sensitive ink film 301 is fixedly attached to the base film 300 through a spacer 302 which is adhesive on both sides, while providing spaces therebetween at locations where the detection devices 31 are formed. In each space, a pressure-sensitive ink layer (epoxy resin) 303 is pasted on the inside surface of the ink film 301 and an electrode pattern 304 of the electrodes 31a and 31b is printed on the inside surface of the base film 300.

Preferably, the detection device 31 is about 0.3 mm in thickness and the film is made of an elastic material such as PEI (polyether imide), so that the load detection sensor unit 3 may be integrated with the air mat 1 the surface of which has a small radius of curvature. The base film 300 and the pressure-sensitive ink film 301 deform when a load weight exerts and cause the electrode pattern 304 and the layer 303 contact each other. An arcuate groove H is formed in the base film 300 to surround the detection device 31, so that the load exerted outside the detection device 31 does not influence the detection device 31. Thus, the electric resistance between the electrodes 31a and 31b varies in accordance with the magnitude of the load applied only to the specific load detection device 31.

The signal processing circuit 32 is integrally formed in the detection sensor unit 3 by fixedly attaching a film 320 to the base film 300 through a spacer 308 which is adhesive on both sides. A large-scale integrated circuit (LSI) 321 of a signal processing circuit is solder-mounted on the base film 320 in a space between the base films 300 and 320. A connector 323 is mounted on the outside surface of the base film 320 and connected to output terminals of the signal processing circuit.

In the signal processing circuit 32, connecting terminals 322 connected to the signal processing circuit are connected to the electrode terminals 306 through anisotropic conductors 307. Each conductor 307 is made of an elastic conductive rubber and pasted with a conductive adhesive. Thus, the signal processing circuit 32 is connected to the detection devices 31 through anisotropic conductors 307 and the signal output lines 5. According to this construction, the output signal lines 5 of the detection devices 31 are restricted from being cut out even if stresses arising from deformation of the base film 300 exerts on the output signal lines 5, because the stresses are minimized by elastic deformation of the anisotropic conductors 307.

Figure 3:
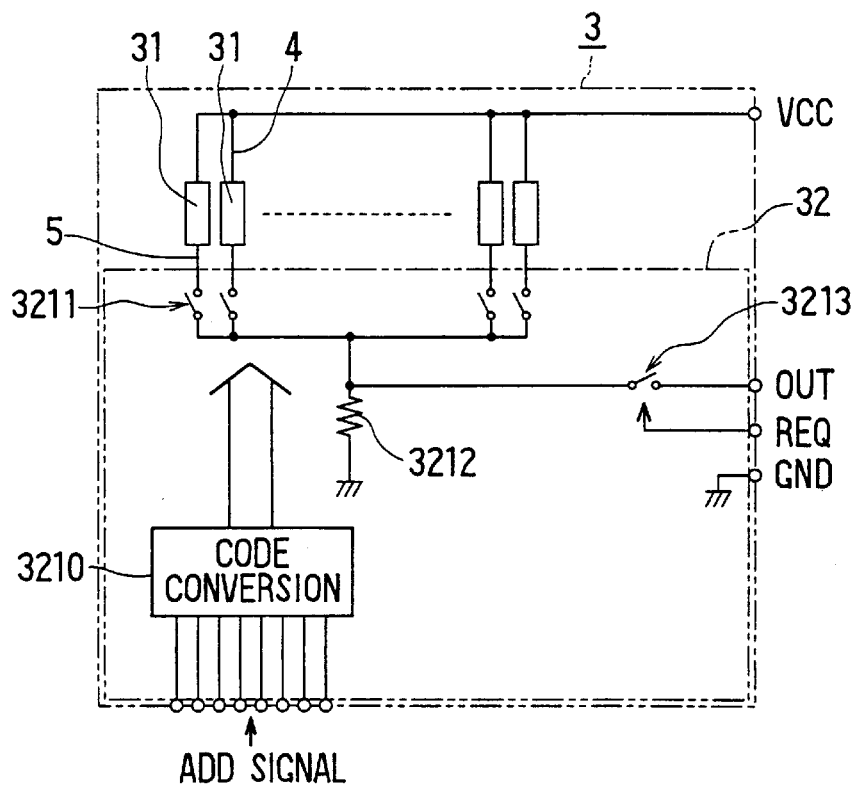
FIG. 3 is a circuit diagram showing an electrical connection in the load detection sensor unit shown in FIG. 1.

The load detection sensor unit 3 has a circuit configuration shown in FIG. 3. The detection devices 31 are supplied with a fixed voltage vcc through the power supply line 4. Further, the detection devices 31 are connected to one end of a load resistor 3212 through a single line connected to the output signal lines 5 through analog switches 3211. The other end of the load resistor 3212 is grounded. The junction between the single line and the load resistor 3212 is connected to an output terminal OUT of the signal processing circuit 32 which is connected to the posture determination unit 100 through a signal output switch 3213.

The analog switches 3211 are connected to a code conversion circuit (switch controller) 3210 which is connected to the posture determination unit 100 and converts binary-coded addresses to corresponding decimal codes. Each decimal code specify one of the analog switches 3211 to be turned on.

When a request signal is applied from the posture determination unit 100 to a request terminal REQ, the signal output switch 3213 is turned on to transmit a voltage signal developed across the resistor 3212 to the output terminal OUT. This voltage signal varies in correspondence with each load-dependent resistance of the detection devices 31 which are connected in sequence to the load resistor 3212 through the analog switches 3211. Thus, by sequentially changing the address codes applied to the conversion circuit 3210, the analog switches 3211 are turned on sequentially to produce the voltage signals indicative of load applied to each detection device 31 on a time-divided basis. It is preferred that the request signal to the output switch 3213 is applied after the voltage from the load resistor 3212 is stabilized, that is, after a delay period from turning on of the analog switches 3211.

As described above, according to this embodiment, the output signals of the detection devices 31 produced in parallel are serialized by the analog switches 3211 and are produced through the single output line. Thus, wiring lines connecting the detection devices 31 can be reduced from 211 to 12, for instance.

The above embodiment may be modified as follows.

For instance, each load detection device may be a capacitive-type or a strain gauge-type as long as it is constructed elastically. The signal processing circuit 32 may be force-fit to the base film 300. Further, the load detection devices 31 and the signal processing circuit 32 may be connected by any connecting members other than the anisotropic conductors 307.

Further, all output signals from the load detection devices 31 need not be transmitted to the external device 100 through a single line. It is still advantageous as long as the number of signal lines between the signal processing circuit 32 and the external device 100 is reduced in comparison with the number of the signal lines connecting the load detection devices 31 and the signal processing circuit 32.

Still further, the external device 100 may also be provided on the base film 320 together with the signal processing circuit 32. In this instance, the external device 100 only determines the sleeping posture and sends the determined posture to a display provided away from the external device.

The present invention should not be limited to the above embodiment and modifications, but may be implemented in various ways without departing from the spirit of the invention.

What is claimed is:

1. A load detection sensor unit for a bedding comprising:
   a sheet made of a film material;
   a plurality of detection devices arranged on the sheet as a part of the bedding for producing output signals variable with respective loads applied thereto by a sleeper, the detection devices each having output signal lines for transmitting the output signals;
   switches for turning on and off transmission of the output signals of the detection devices, the switches being mounted on the sheet and connected to the output signal lines of the respective detection devices;
   a signal processing circuit for controlling the switches so as to serialize the output signals of the detection devices, the signal processing circuit being mounted on the sheet and connected to the switches;
   an electrical unit disposed outside the bedding for detecting the respective loads applied to the bedding from the output signals produced by the detection devices; and
   a single signal line connecting the signal processing circuit to the electrical unit,
   wherein a serialized output signal of the output signals of the detection devices is transmitted to the electrical unit through the single signal line.

2. The load detection sensor unit of claim 1, further comprising:
   a load resistor connected to the single signal line to produce a voltage signal developed thereacross as the output signals of the detection devices.

3. The load detection sensor unit of claim 1, further comprising:
   a conductive pattern formed on the sheet as the output signal lines of the detection devices.

4. The load detection sensor unit of claim 3, wherein the signal processing circuit includes:
  a second sheet;
  an electrical circuit mounted on the second sheet;
  connecting terminals formed on the second sheet and connected to the electrical circuit; and
  an elastic conductive member located between the first sheet and the second sheet to connect the conductive pattern on the first sheet and the connecting terminals on the second sheet therethrough.

5. A load detection sensor unit for a bedding comprising:
  a first film sheet placed on the bedding;
  a second film sheet fixedly attached to the first film sheet;
  a plurality of detection devices attached to the first film sheet at different locations for producing output signals variable with respective loads applied thereto through output signal lines;
  a signal processing circuit attached to the second film sheet and having signal input lines and a single output line, the signal processing circuit including a plurality of switches connected between the input signal lines and the single output line and a switch controller for sequentially turning on the switches to transmit the output signals of the detection devices to the single output line as a series of the output signals; and
  elastic conductive members disposed between the first film sheet and the second film sheet and connecting the output signal lines of the detection devices and the input signal lines of the signal processing circuit.

6. The load detection sensor unit of claim 5, further comprising:
  a third film sheet fixedly attached to the first film sheet at a location different from the second film sheet;
  an elastic spacer disposed between the first film sheet and the third film sheet to provide spaces between the first film sheet and the third film sheet,
  wherein the detection devices are fixedly mounted within the spaces, respectively.

7. A sensor array for detecting a load applied to a bedding, comprising:
  a plurality of detection devices arranged as a part of the bedding, wherein each of said plurality of detection devices produces output signals variable with a load applied thereto;
  signal output means for carrying output signals from said plurality of detection devices; and
  a plurality of switches for turning on and off transmission of said output signals, wherein said switches are located in the bedding.

8. A sensor array for detecting a load applied to a bedding, comprising:
  a plurality of detection devices arranged as a part of the bedding, wherein each of said plurality of detection devices produces output signals variable with a load applied thereto;
  a plurality of switches for turning on and off transmission of said output signals, wherein said switches are located in the bedding;
  a signal processing circuit located in the bedding for controlling said switches so as to serialize said output signals of said detection devices; and
  a single signal line for carrying said output signals of said detection devices outside the bedding one by one in sequence as a serialized signal of said signal processing circuit.

9. The sensor array of claim 8, further comprising:
  a posture determination unit that determines a posture of a sleeper from said serialized signal of said signal processing circuit, wherein said posture determination unit is disposed outside the bedding.

10. The sensor array of claim 9, further comprising:
  an air pump that is controlled by said posture determination unit and that regulates an inside pressure of bedding air cells with respect to each part of said sleeper based on said posture.

11. The sensor array of claim 8, wherein said plurality of switches and said plurality of detection devices are located on a first layer in the bedding.

12. The sensor array of claim 8, wherein said plurality of switches and said plurality of detection devices are located on a same layer in the bedding.

13. The sensor array of claim 8, wherein said plurality of switches are located on layer other than a layer on which said plurality of detection devices are located in the bedding.

* * * * *